(12) United States Patent
Song (10) Patent No.: US 11,633,092 B2
(45) Date of Patent: Apr. 25, 2023

(54) LARYNGEAL MASK AIRWAY FOR SEDATIVE ENDOSCOPY

(71) Applicant: CATHOLIC UNIVERSITY OF DAEGU INDUSTRY ACADEMIC COOPERATION FOUNDATION, Gyeongsan-si (KR)

(72) Inventor: Seokyoung Song, Daegu (KR)

(73) Assignee: CATHOLIC UNIVERSITY OF DAEGU INDUSTRY ACADEMIC COOPERATION FOUNDATION, Gyeongsan-si (KR)

( * ) Notice: Subject to any disclaimer, the term of this patent is extended or adjusted under 35 U.S.C. 154(b) by 935 days.

(21) Appl. No.: 16/473,827

(22) PCT Filed: Mar. 3, 2017

(86) PCT No.: PCT/KR2017/002326
§ 371 (c)(1),
(2) Date: Jun. 26, 2019

(87) PCT Pub. No.: WO2018/124387
PCT Pub. Date: Jul. 5, 2018

(65) Prior Publication Data
US 2019/0350451 A1    Nov. 21, 2019

(30) Foreign Application Priority Data

Dec. 28, 2016  (KR) .................... 10-2016-0180911

(51) Int. Cl.
*A61B 1/267*    (2006.01)
*A61B 1/00*     (2006.01)
(Continued)

(52) U.S. Cl.
CPC .......... *A61B 1/267* (2013.01); *A61B 1/00154* (2013.01); *A61B 1/2733* (2013.01); *A61B 1/32* (2013.01); *A61M 16/0434* (2013.01)

(58) Field of Classification Search
CPC .... A61B 1/267; A61B 1/2733; A61B 1/00154
See application file for complete search history.

(56) References Cited

U.S. PATENT DOCUMENTS

2012/0283513 A1    11/2012  Leeflang et al.
2016/0192829 A1*   7/2016   Poulsen ............ A61M 16/0497
                                                             600/115

FOREIGN PATENT DOCUMENTS

JP    2011-229926 A    11/2011
JP    2011-255095 A    12/2011
(Continued)

*Primary Examiner* — Olivia C Chang
(74) *Attorney, Agent, or Firm* — FisherBroyles, LLP; Joseph Hyosuk Kim (57) ABSTRACT

The present invention provides laryngeal mask airway for sedative endoscopy, including: a laryngeal mask/endoscope guide unit which is positioned in a larynx region inlet through a patient's oral cavity and guides a supply of air to a respiratory tract and insertion of an endoscope into an esophagus; an airway unit which is connected to the laryngeal mask/endoscope guide unit to supply air to the patient's respiratory tract and to allow the patient's breathing state to be visually checked; a mouthpiece unit which is installed outside the airway unit and fixed between the patient's teeth to protect a tube of the airway and an endoscopic probe inserted into the oral cavity; and an indication end which is positioned at a portion of the mouthpiece positioned outside the oral cavity and moves in accordance with the patient's breathing state to allow spontaneous breathing to be checked, such that the patient's safe airway may be ensured, the insertion of the endoscopic probe and the procedure may be smoothly performed, the patient's spontaneous breathing (Continued)

is easily checked even in a dark space, and as a result, the endoscopy may be safely performed.

20 Claims, 6 Drawing Sheets

(51) Int. Cl.
    *A61B 1/273*     (2006.01)
    *A61B 1/32*     (2006.01)
    *A61M 16/04*     (2006.01)

(56) References Cited

FOREIGN PATENT DOCUMENTS

| | | |
|---|---|---|
| KR | 10-2009-0067778 A | 6/2009 |
| KR | 10-2016-0094366 A | 8/2016 |

\* cited by examiner

LARYNGEAL MASK AIRWAY FOR SEDATIVE ENDOSCOPY

CROSS REFERENCE TO RELATED APPLICATIONS AND CLAIM OF PRIORITY

This patent application is a National Phase application under 35 U.S.C. § 371 of International Application No. PCT/KR2017/002326, filed Mar. 3, 2017, which claims priority to Korean Patent Application No. 10-2016-0180911 filed Dec. 28, 2016, entire contents of which are incorporated herein by reference.

TECHNICAL FIELD

The present invention relates to a laryngeal mask airway which secures a respiratory tract and is used to check for spontaneous breathing in order to prevent a respiratory failure caused by insertion of an endoscopic probe and an observing operation during esophagogastroduodenoscopy under sedation using a sedative.

BACKGROUND ART

Typically, esophagogastroduodenoscopy is an examination procedure of checking for abnormalities in a gastrointestinal tract while inserting an endoscope into a stomach or a duodenum through an esophagus via an oral cavity.

Examinees avoid the esophagogastroduodenoscopy because of the inconvenience caused by pain when swallowing the endoscope and because of foreign body feeling felt by the examinees while the endoscope passes through the gastrointestinal tract via the esophagus.

In general, in order to facilitate the examination of the intestine, a sedative is administered to the examinee and then the endoscopy is performed under sedation.

The endoscopy under sedation is mostly desired by patients, but there is a problem in that accidents caused by respiratory failures often occur due to excessive sedation during the procedure in accordance with individual differences in sedative response and difficulty of the procedure.

The endoscopy is a comparatively simple procedure that takes 10 to 20 minutes, but the very difficult endoscopy sometimes takes one or more hours.

In this case, another risk occurs and time, human and material costs are incurred to perform general anesthesia through invasive endotracheal intubation.

As a solution for solving the problem with the endoscopy under sedation, a laryngeal mask airway is used to perform the endoscopy in the related art.

However, the laryngeal mask airway structurally has a large volume that occupies the oral cavity and the esophagus, which causes significant inconvenience to practitioners, and as a result, the practitioners are reluctant to use the laryngeal mask airway.

Airways having other forms also provide passing windows through which endoscopic probes are inserted, but these airways also cause the inconvenience to the practitioners.

Korean Patent Application Laid-Open No. 10-2005-0098256 has proposed a laryngeal mask airway device (hereinafter, referred to as the 'prior art').

According to the proposed prior art, in an airway tube 510 for a laryngeal mask airway device, the laryngeal mask airway device includes an expandable cuff 134 or is formed in the form of gel, the cuff 134 or the gel portion defines a central opening and may be inserted into an insertion location in a patient's body through an oral cavity. When the cuff 134 or the gel portion is expanded, the cuff 134 or the gel portion surrounds the patient's glottis opening at the insertion location, and the airway tube includes a wall having flexibility. When the airway tube has an inserted shape, the wall includes a reduced thickness section in a section of the tube which is contracted or extended. A cross section of the wall has an outer circumference 510-*o*, the outer circumference 510-*o* includes a curved portion 510-*c* and a linear portion 510-1, and the linear portion 510-1 connects both ends A and B of the curved portion 510-*c*.

However, the above-mentioned prior art is cumbersome because it is impossible to visually determine whether the patient breathes and thus it is necessary to touch the respiratory with hand or to approximate the ear to the patient's nose. In particular, in the dark place, such a direct determination method is not only inconvenient but also has a problem in that the time when the patient needs to be promptly treated is missed.

DISCLOSURE

Technical Problem

An object of the present invention is to reduce a volume of a back region for tight attachment of a mask to a larynx region which is structural vulnerability of a laryngeal mask airway in the related art, to assist the tight attachment to the larynx region by mounting a semi-circular support band, and to allow an endoscopic probe to pass through a ring.

Another object of the present invention is to allow a tube of an airway, through which air flows, to be provided at an eccentric position of a mask piece, to allow the tube to pass through a mouthpiece along a wall in an oral cavity and then be positioned in a direction toward a face, and to prevent the tube from hindering endoscopy such that the procedure is enabled in an environment identical to an environment in which no laryngeal mask airway is present.

Still another object of the present invention is to provide a convenience of operating a probe.

Yet another object of the present invention is to allow a practitioner to easily check a breathing state in accordance with a movement of an indicator depending on whether the patient spontaneously breathes through a breathing monitoring window of a tube exposed to the outside of the patient's mouth, in consideration of the nature of endoscopy performed in a dark room.

Technical Solution

The present invention provides laryngeal mask airway for sedative endoscopy, including: a laryngeal mask/endoscope guide unit which is inserted into a patient's respiratory tract to ensure an opened state of the respiratory tract and to guide insertion of an endoscope; an airway unit which is connected to a laryngeal mask piece of the laryngeal mask/endoscope guide unit to supply oxygen to the patient's respiratory tract and to allow the patient's breathing state to be visually checked; and a mouthpiece unit which is installed outside the airway unit to protect an airway tube and an endoscopic probe inserted into an oral cavity.

The laryngeal mask/endoscope guide unit may include: the laryngeal mask piece which is inserted into the patient's oral cavity and mounted in a larynx region so as to divide the respiratory tract and an esophagus, such that an end of the tube from the airway unit is opened toward the larynx region; a support band which has a semi-circular shape and protrudes from a rear surface of the laryngeal mask piece to expand an esophagus inlet; and an endoscope guide hole which provides a space that allows the endoscopic probe to pass a rear surface of the laryngeal mask piece on which the support band is installed.

The airway unit may have the tube which is coupled to an air inlet hole of the laryngeal mask piece of the laryngeal mask/endoscope guide unit and has an inlet hole through which air is guided from the outside of the patient's oral cavity to the laryngeal mask piece in the oral cavity, and the tube may have a variable end which is bent at a portion connected to the laryngeal mask piece so that the variable end comes into contact with an inner wall of the oral cavity, and an indication end which is bent at a portion exposed to the outside of the oral cavity so as to allow the patient's spontaneous breathing to be checked.

At a free end of the tube, there may be further provided: a breathing indicating hole which is formed in parallel with the inlet hole; a first hole which is formed to be connected to the inlet hole at one side of the breathing indicating hole so that oxygen is introduced when the patient breathes in; a second hole which is formed to be connected to the inlet hole at the other side of the breathing indicating hole so that oxygen is discharged when the patient breathes out; and a mover which is inserted into the breathing indicating hole and moved by a flow of oxygen generated when the patient breathes in and out.

The bent portion of the airway unit may have a catching protrusion that maintains a coupled state with the laryngeal mask piece of the laryngeal mask/endoscope guide unit, and a catching groove, which is inserted into the inlet hole of the tube and caught by the laryngeal mask piece, may be further provided in the laryngeal mask piece.

The support band of the laryngeal mask/endoscope guide unit may have shrinkable and restorable shrinkable holes formed at both ends of the support band separable from the laryngeal mask piece, and has catching pieces formed on outer surfaces of the shrinkable holes so as to be coupled to a guide piece, and a fixing hole having catching projections by which both ends of the support band shrunk and inserted are caught may be provided in the guide piece.

In the laryngeal mask piece of the laryngeal mask/endoscope guide unit, a portion coupled to the bent portion of the airway may have a thickness greater than a thickness of a support piece coupled to the support band, such that a thick portion of the laryngeal mask/endoscope guide unit, which is mounted in the patient's respiratory tract, may be in close contact with the patient's larynx region cover.

Advantageous Effects

According to the present invention, it is possible to perform esophagogastroduodenoscopy and other facial surgery under more appropriate and safe sedation.

There is an advantage in that it is possible to safely ensure an airway and check spontaneous breathing when there is a difficulty of a procedure or the patient's safety is threatened due to respiratory failure during inappropriate esophagogastroduodenoscopy under sedation.

It is possible to reduce a volume of a back region for tight attachment of a mask to a larynx region which is structural vulnerability of a laryngeal mask airway in the related art, and to assist the tight attachment to the larynx region by mounting the tunnel-shaped support band.

The endoscopic probe passes through the esophagus by being guided by the support band, such that there is a convenience of operating the probe unlike the related art in which a tool separately having a passing tube for an endoscopic probe from the outside of the mouth makes it difficult for a practitioner to operate a probe.

There is a convenience of checking the patient's spontaneous breathing through the breathing monitoring window of the tube exposed to the outside of the oral cavity, in consideration of the nature of endoscopy performed in a dark room.

DESCRIPTION OF DRAWINGS

FIGS. 7A-7B show the laryngeal mask piece with or without the support band.

MODES OF THE INVENTION

Particular exemplary embodiments for carrying out the present invention will be described with reference to the accompanying drawings.

Hereinafter, the exemplary embodiments of the present invention will be described in detail with reference to the accompanying drawings so that those skilled in the art to which the present invention pertains may easily carry out the present invention.

Figure 1:
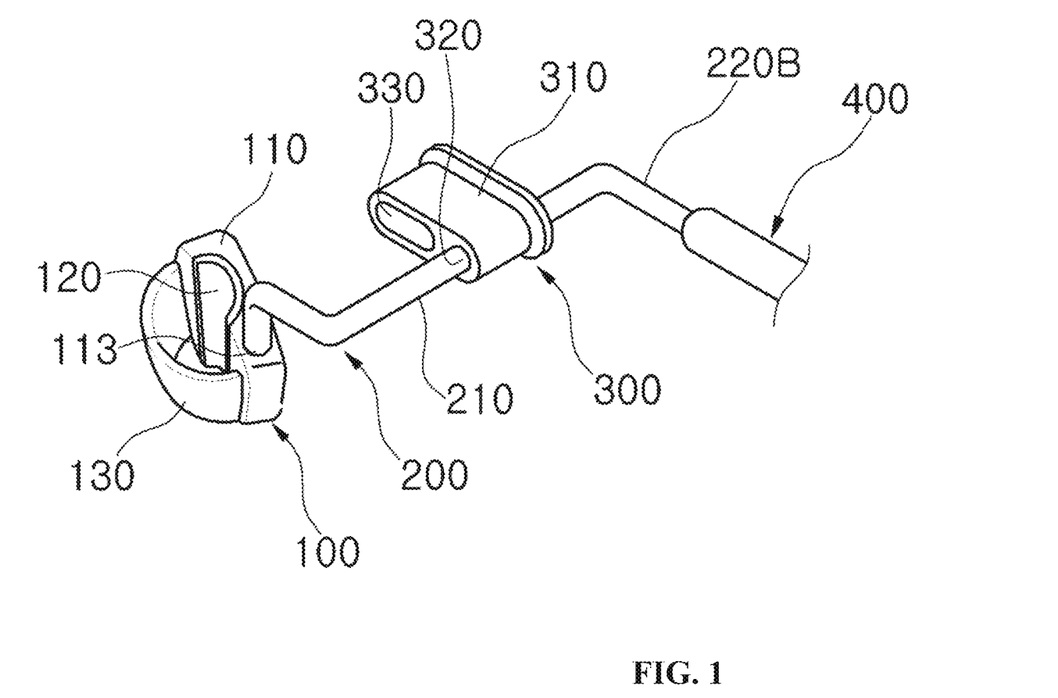
FIG. 1 is a perspective view of a laryngeal mask airway for sedative endoscopy to which the present invention is applied.

FIG. 1 is a perspective view illustrating a laryngeal mask airway for endoscopy under sedation to which the present invention is applied.

The laryngeal mask airway (ELMA) for endoscopy under sedation to which the present invention is applied includes: a laryngeal mask/endoscope guide unit 100 which is inserted into a patient's larynx inlet to ensure an opened state of a respiratory tract and guide insertion of an endoscopic probe into an esophagus; an airway unit 200 which is connected to a laryngeal mask piece 110 of the laryngeal mask/endoscope guide unit 100 to allow outside air to be supplied to the patient's respiratory tract and visually indicating the patient's breathing state; a tube 210 of the airway unit 200 which is positioned in the patient's oral cavity inlet and allows outside air to be supplied to the respiratory tract; and a mouthpiece unit 300 which fixes a length of the endoscopic probe which is inserted into the oral cavity during the endoscopy and divides teeth so that the laryngeal mask airway is not pressed and tangled as the teeth occlude.

Figures 2A, 2B, 2C:
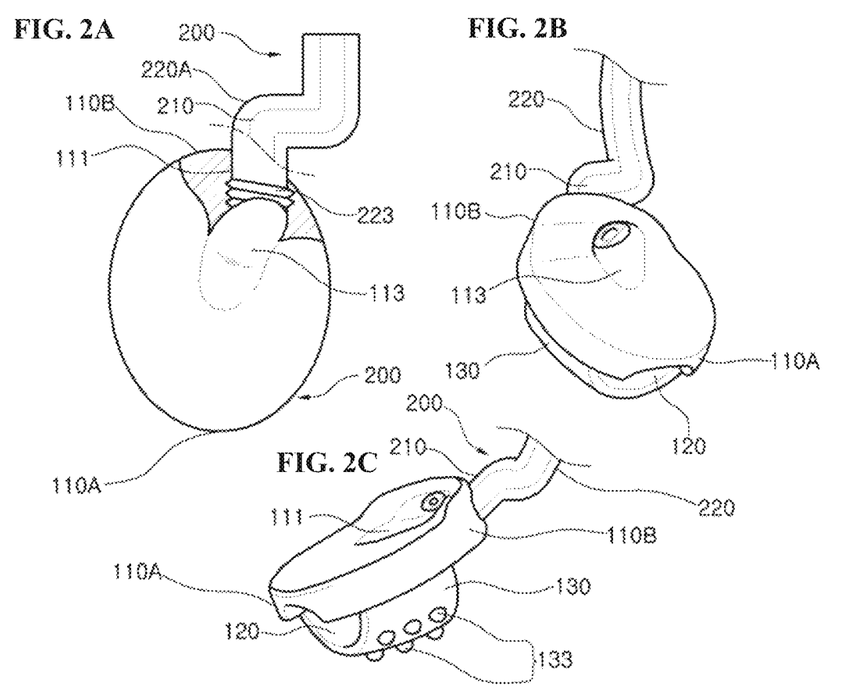
FIGS. 2A-2C are (a) a rear view, (b) a rear perspective view, and (c) an inclined perspective view of laryngeal mask airway for sedative endoscopy to which the present invention is applied.

FIG. 2 is (a) a rear view, (b) a rear perspective view, and (c) an inclined perspective view of the laryngeal mask airway for endoscopy under sedation to which the present invention is applied.

Among the constituent elements according to the present invention, the laryngeal mask/endoscope guide unit 100 has the laryngeal mask piece 110 which is inserted into the patient's oral cavity and has a thickness and a shape to divide the respiratory tract and the esophagus in the larynx region.

Figure 4:
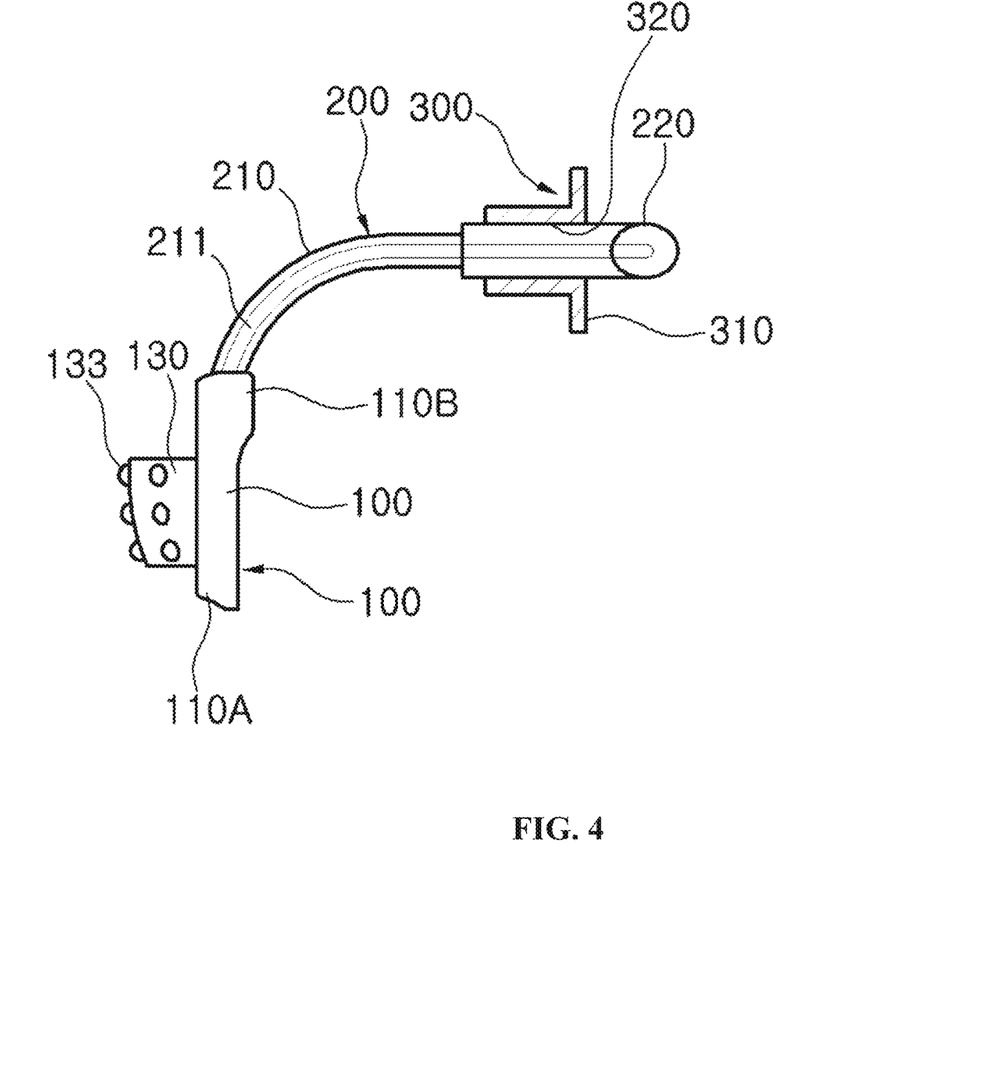
FIG. 4 is a state view of the laryngeal mask airway for sedative endoscopy to which the present invention is applied when viewed from the front side.

The laryngeal mask piece 110 includes a tip portion 110A which is inserted into the oral cavity and positioned in the larynx region, and a rear end portion 110B which is positioned in the respiratory tract and the esophagus. A thickness of the rear end portion 110B is greater than a thickness of the tip portion 110A so that the respiratory tract and the esophagus are divided and the tip portion 110A is well in contact with the larynx region to prevent a leakage of air (FIG. 4).

A tube coupling hole 111 in which the airway unit 200 is installed is formed in the thick rear end portion 110B of the laryngeal mask piece 110.

The tube coupling hole 111 penetrates from the thick rear end portion 110B to the thin tip portion 110A, such that when the penetrating tube coupling hole 111 reaches the tip portion 110A, the tube coupling hole 111 is exposed because of the small thickness, and an outer surface of the tip portion 110A is concavely recessed, and as a result, an air inlet hole 113 is formed.

The tube coupling hole 111 and the air inlet hole 113 define a single passageway, such that outside air is introduced in a direction from a position of the oral cavity inlet to the larynx region.

Further, an endoscope guide hole 120 is provided at a position opposite to the position at which the tube coupling hole 111 and the air inlet hole 113 are formed. The endoscope guide hole 120 is formed as a groove concavely recessed at a central portion of an outer surface of the laryngeal mask piece 110 in a direction from the oral cavity inlet to the esophagus such that the insertion of the endoscopic probe is smoothly guided through the oral cavity toward the esophagus.

Figure 3:
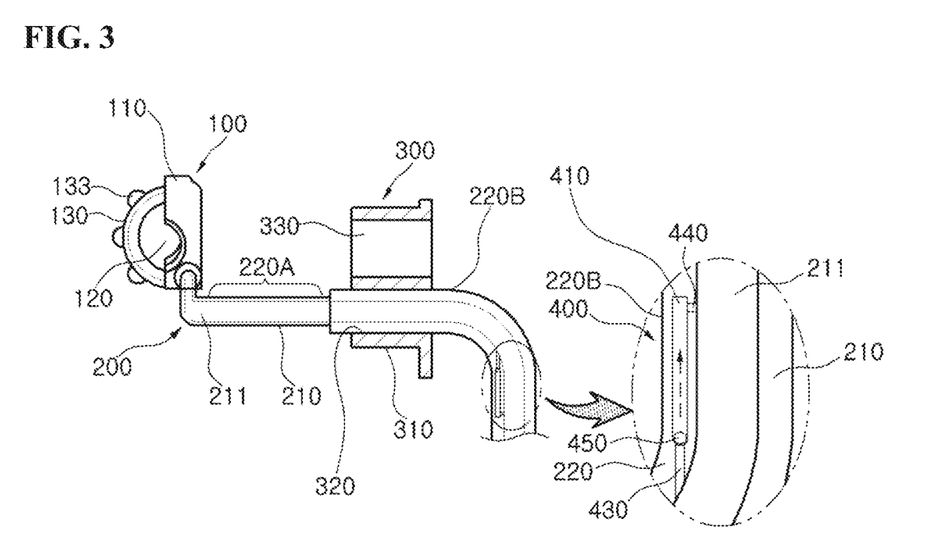
FIG. 3 is a state view of laryngeal mask airway for sedative endoscopy to which the present invention is applied when viewed in a plan view.

Further, the support band 130, which is configured to guide the endoscopic probe moving along the endoscope guide hole 120 and prevent the endoscopic probe from deviating from the endoscope guide hole 120, is installed at both sides of the endoscope guide hole 120. The support band 130 is formed in a semi-circular band shape so that an esophagus inlet is expanded when the support band 130 comes into contact with the esophagus inlet. An outer surface of the support band 130 is formed to be inclined so that the support band 130 is easily inserted into the esophagus inlet (FIG. 3).

The airway unit 200 is installed in the tube coupling hole 111 of the laryngeal mask piece 110. The airway unit 200 is configured to allow air to be supplied from the outside of the patient's oral cavity to the patient's respiratory tract and includes a hose-shaped tube 210.

An inlet hole 211 through which the air flows is provided in the hose-shaped tube 210, and a catching protrusion 212 is formed to allow one end of the tube 210 to be stably coupled to the tube coupling hole 111 of the laryngeal mask piece 110.

The tube 210 of the airway unit 200 should not hinder the operation of the endoscopic probe that enters or exits the patient's oral cavity and digestive system in the state in which the tube 210 is coupled to the laryngeal mask piece 110. Therefore, the tube coupling hole 111 formed in the rear end portion 110B of the laryngeal mask piece 110 is formed at a position eccentric in the right direction of the laryngeal mask piece 110.

Therefore, the tube 210 of the airway unit 200 coupled to the tube coupling hole 111 is installed at the right position eccentric from the rear end portion 110B of the laryngeal mask piece 110, and as a result, the tube 210 is positioned at the right position in the oral cavity.

Figure 5:
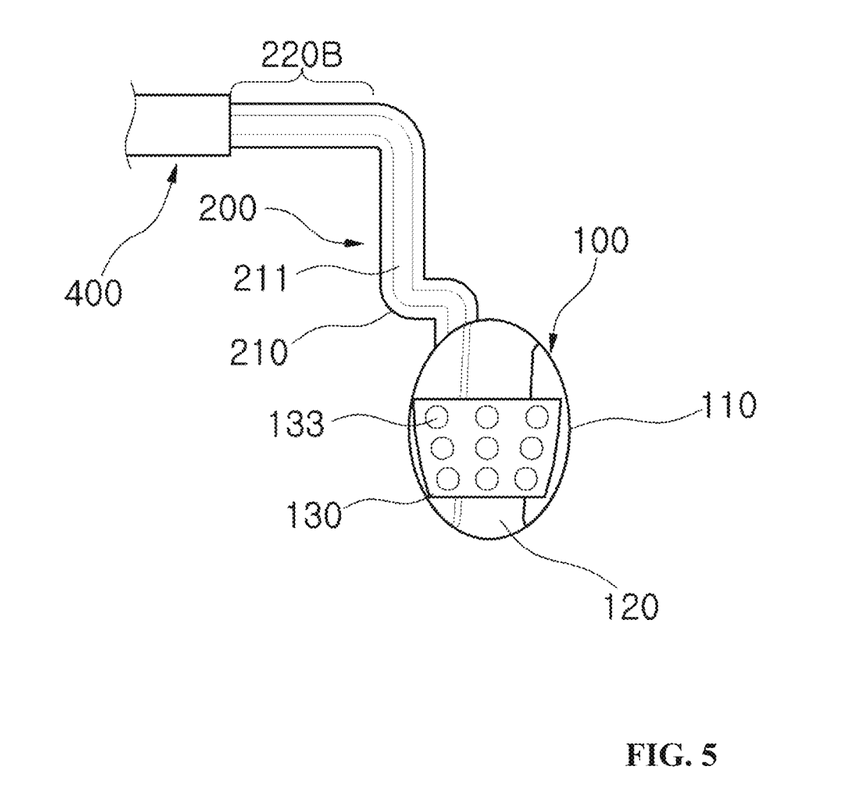
FIG. 5 is a state view of the laryngeal mask airway for sedative endoscopy to which the present invention is applied when viewed from the left side.

FIG. 3 is a state view of the laryngeal mask airway for endoscopy under sedation to which the present invention is applied when viewed in a plan view, FIG. 4 is a state view of the laryngeal mask airway for endoscopy under sedation to which the present invention is applied when viewed from the front side, and FIG. 5 is a state view of the laryngeal mask airway for endoscopy under sedation to which the present invention is applied when viewed from the left side.

The support band 130, which has a semi-circular band shape and comes into contact with the esophagus inlet, is formed on the laryngeal mask piece 110 positioned in the larynx inlet, and the support band 130 is formed to be inclined as illustrated in FIGS. 4 and 5.

The reason why the support band 130 has a semi-circular band shape and is formed to be inclined is that the support band 130 is easily inserted into the esophagus inlet to expand the esophagus inlet.

In addition, in order to make friction when the support band 130 comes into contact with a mucous membrane of the esophagus in the state in which the support band 130 is inserted into the esophagus inlet, multiple protrusions 133 protrude from a surface of the support band 130.

The tube 210 of the airway unit 200 installed in the tube coupling hole 111 of the laryngeal mask piece 110 has softness to meet the purpose of the medical instrument, and the mouthpiece unit 300 is formed outside the tube 210 to protect the tube 210.

The mouthpiece unit 300 includes a mouthpiece 310 which is made of an elastic material and has a thickness that prevents upper and lower teeth from coming into contact with one another in the oral cavity and at a lip position, and the mouthpiece 310 is made of a soft material to protect the tube 210. A tube hole 320 and an endoscope hole 330 are penetratingly formed at a center of the mouthpiece 310.

The tube hole 320 is formed at a position eccentric from the center of the mouthpiece 310 in a direction in which the mouthpiece 310 is inserted into the oral cavity. The endoscope hole 330 is formed at the center position of the mouthpiece 310.

The tube 210 of the airway unit 200 is inserted into the tube hole 320, and the endoscopic probe is inserted into the endoscope hole 330, such that the endoscopic probe penetrates the center position of the mouthpiece unit 300 and the center position of the laryngeal mask piece 110, and the tube 210 penetrates the eccentric position of the mouthpiece unit 300 and is coupled to the tube coupling hole 111 of the laryngeal mask piece 110. Since the tube hole 320 and the endoscope hole 330 are separately positioned, the tube 210 and the endoscopic probe are positioned in the oral cavity so as not to hinder each other, thereby facilitating the operation of the endoscopic probe.

Because the laryngeal mask/endoscope guide unit 100 is mounted in the oral cavity in a state in which the patient is under conscious sedation, a breathing monitoring window 400 is formed in the tube 210 of the airway unit 200 in order to monitor whether the patient smoothly breathes during a diagnosis procedure using the endoscopic probe (FIG. 3).

The breathing monitoring window 400 may be formed in a longitudinal direction of the tube 210 of the airway unit 200, that is, at an indication end 220B positioned outside the oral cavity.

The breathing monitoring window 400 protrudes from an outer circumferential surface of the tube 210 and has a breathing indicating hole 410 formed in parallel with the inlet hole 211, and a first hole 430 is formed at one side of the breathing indicating hole 410 and connected to the inlet hole 211.

A second hole 440 is formed at the other side of the breathing indicating hole 410 and connected to the inlet hole 211.

An indicator 450, which moves in accordance with a movement of air caused when the patient breathes in and out, is provided in the breathing indicating hole 410.

In order to increase visibility of the indicator 450 in the dark place, the indicator 450 itself may be made of a light emitting material or a light storing material or a light emitting material may be attached to a part of a surface of the indicator 450.

Therefore, a part of air, which is introduced along the inlet hole 211 when the patient breathes in, is introduced into the breathing indicating hole 410 through the first hole 430, and a part of air, which is discharged along the inlet hole 211 when the patient breathes out, is introduced into the breathing indicating hole 410 through the second hole 440.

In this case, the movement state of the indicator 450 is visually ascertained in accordance with the direction in which the air is introduced into the breathing indicating hole 410 through the first hole 430 and the second hole 440, such that it is possible to determine whether the patient spontaneously breathes. Therefore, it is possible to very clearly ascertain whether the patient properly breathes under a condition in which the insertion of the endoscopic probe is performed in a dark environment.

When carrying out the present invention, a variable end 220A of the tube 210, which is positioned in the oral cavity, is bent based on the mouthpiece unit 300 installed on the tube 210 of the airway unit 200 so as to allow the tube 210 to come into contact with a surface of a right wall in the oral cavity, thereby maximally widening a space of the oral cavity. The indication end 220B of the airway unit 200 may also be bent so as not to hinder the endoscopy procedure.

According to the exemplary embodiment, the tube 210 may be sufficiently bent at a position so as not to hinder the insertion of the endoscopic probe and the procedure in accordance with the patient's posture during diagnosis.

The bent portion of the variable end 220A comes into close contact with the sidewall of the oral cavity, and the indication end 220B is bent to the extent that the indication end 220B does not come into contact with the patient's face, such that it is possible to smoothly operate the endoscopic probe and to ascertain whether the patient spontaneously breathes during the procedure.

Figure 6:
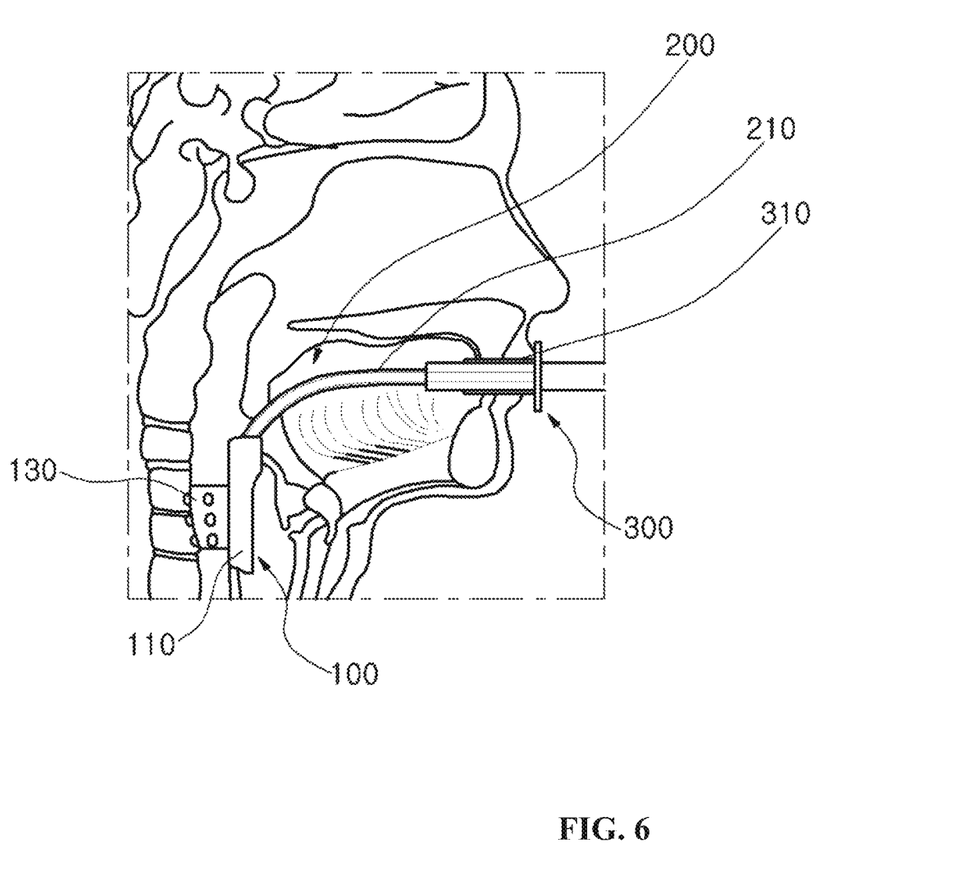
FIG. 6 is an exemplified cross-sectional view illustrating a state in which the laryngeal mask airway according to the present invention is mounted on a patient.

That is, a state in which the laryngeal mask airway (ELMA) according to the present invention is applied to the endoscopy will be described as an example. The patient to be subjected to the endoscopy lies on his/her left side and goes under sedation in the state in which the mask piece 110 according to the present invention is inserted into the oral cavity and reaches the respiratory tract and the esophagus in the oral cavity.

The endoscopy practitioner inserts the endoscopic probe into the endoscope hole 330 of the mouthpiece 310 stuck in the patient's mouth and inserts the endoscopic probe into the oral cavity.

The endoscopic probe inserted into the oral cavity is inserted into the digestive system while entering the esophagus inlet expanded by the support band 130 and the endoscope guide hole 120 of the laryngeal mask piece 110.

During the process of medically determining the observation through the endoscopy while inserting the endoscopic probe into the digestive system, the endoscopic probe returns to the suspicious position for re-observation, and thus the endoscopic probe is repeatedly extended and retracted. However, since the tube 210 of the airway unit 200 and the endoscopic probe are divided by the tube hole 320 and the endoscope hole 330 of the mouthpiece 310, the endoscopic probe and the tube 210 do not interfere with each other.

In addition, during the process of inserting the endoscopic probe into the digestive system through the patient's oral cavity as described above, the endoscopy practitioner determines whether the patient spontaneously breathes by monitoring a motion of the indicator 450 through the breathing monitoring window 400 provided at the indication end 220B of the tube 210 which is bent toward the patient's face.

In particular, the tube 210, which is positioned in the space of the oral cavity between the mouthpiece 310 positioned in the oral cavity inlet and the laryngeal mask piece 110 installed in the larynx region, is bent by the variable end 220A and comes into contact with the surface of the right wall in the space of the patient's oral cavity, and the tube 210 for supplying air and the moving endoscopic probe do not interfere with each other by the configuration in which the tube hole 320 and the endoscope hole 330 are divided. As a result, during the process of performing the endoscopy on the patient lying on his/her left side, the tube 210 in the oral cavity does not hinder the motion of the endoscopic probe, such that the endoscopy may be smoothly performed.

The tube 210 of the airway unit 200, which supplies outside air to the patient's respiratory tract during the endoscopy, may be bent to be close to the indication end 220B positioned outside the oral cavity, that is, to the patient's face, such that the tube 210 does not hinder the procedure operation of the endoscopy practitioner. Further, the endoscopy practitioner easily ascertains whether the patient still spontaneously breathes by often checking the motion of the indicator 450 provided in the breathing monitoring window 400.

Figure 7A:
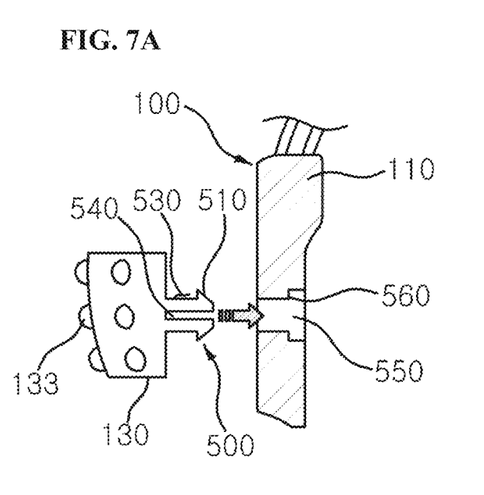
FIG. 7A is a view illustrating a state in which a support band according to another exemplary embodiment of the present invention is separated from a laryngeal mask piece.
Figure 7B:
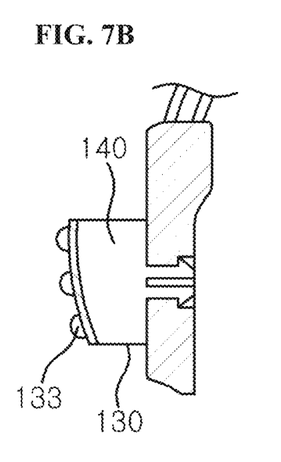
FIG. 7B is a view illustrating a state in which the support band is coupled to the laryngeal mask piece.

In addition, as illustrated in FIG. 7, the support band 130 may be configured to be detachable when carrying out the present invention.

FIG. 7A is a view illustrating a state in which the support band according to the present invention is separated from a guide piece, and FIG. 7B is a view illustrating a state in which the support band is coupled to the guide piece.

The support band 130, which is separable from the guide piece 110 of the endoscope guide unit 100, has shrinkable and restorable shrinkable holes 540 formed at both ends of the support band 130 so as to be assembled to the guide piece 110, and catching pieces 510 each having an arrowhead shape protrude from outer surfaces of the shrinkable holes 540 so as to be coupled to fixing holes 550 formed in the guide piece 110.

Further, catching projections 560, by which the catching pieces 510 are caught, are formed in the fixing hole 550 of the guide piece 110.

The catching pieces 510 are retracted inward by the cut shrinkable holes 540 when both ends of the support band 130 are pushed, such that the catching pieces 510 may enter and exit the fixing holes 550 of the guide piece 110. When the force for pushing both ends of the support band 130 is eliminated, the catching pieces 510 return to the original positions, and the catching pieces 510 are caught by the catching projections 560 in the fixing holes 550, such that the support band 130 is installed to protrude from the surface of the guide piece 110.

While the exemplary embodiments of the present invention have been described above with reference to the accompanying drawings, the present invention is not limited to the exemplary embodiments disclosed above but will be implemented in various different forms, and those skilled in the art will understand that the present invention may be implemented in any other specific form without changing the technical spirit or the essential feature of the present invention. Therefore, it should be understood that the above-described exemplary embodiments are illustrative in all aspects and do not limit the present specification.

The invention claimed is:

1. A laryngeal mask airway unit for sedative endoscopy, comprising:
    a laryngeal guide unit which includes a laryngeal mask piece configured to be positioned in a patient's larynx inlet, and a support band attached to and that extends away from the laryngeal mask piece, the support band being configured to ensure an opened state of a patient's respiratory tract and configured to guide insertion of an endoscopic probe into a patient's esophagus;
    an airway unit which includes a tube connected to the laryngeal mask piece and configured to supply outside air to the patient's respiratory tract; and
    a mouthpiece unit that is separate from the laryngeal guide unit and that is configured to be positioned between a patient's teeth, wherein the tube of the airway unit extends through a first passageway in the mouthpiece unit and wherein the mouthpiece unit includes a second passageway configured to receive an endoscopic probe, wherein the mouthpiece unit is configured to protect, from a patient's teeth, the tube of the airway unit and an endoscopic probe extending though the second passageway, and wherein the mouthpiece unit is configured to separate the tube of the airway unit and an endoscopic probe so that the tube and the endoscopic probe do not interfere with each other during endoscopy.

2. The laryngeal mask airway unit of claim 1, wherein the laryngeal guide unit has a flat elliptical plate shape and comprises:
    a tube coupling hole formed in a rim of the laryngeal mask piece, wherein the tube of the airway unit is installed in the tube coupling hole;
    an air inlet hole which is formed as a concave groove extended from the tube coupling hole and which is exposed on an outer surface of the laryngeal mask piece to allow outside air supplied from the tube to be supplied to a patient's oral cavity and the respiratory tract; and
    an endoscope guide hole which is concavely formed on a surface of the laryngeal mask piece opposite to the air inlet hole, wherein the endoscope guide hole is configured to guide the insertion of an endoscopic probe inserted into a patient's oral cavity in a direction toward the patient's esophagus.

3. The laryngeal mask airway unit of claim 1, wherein the support band of the laryngeal guide unit has a semi-circular shape, wherein an outer surface of the support band is formed to be inclined in a direction toward a patient's esophagus and wherein multiple protrusions protrude from an outer surface of the support band, the protrusions being configured to increase friction with a patient's mucous membrane of the esophagus and to thereby minimize motion of the laryngeal guide unit relative to a patient's mucous membrane of the esophagus.

4. The laryngeal mask airway unit of claim 2, wherein the airway unit includes:
    a catching protrusion formed at an end of the tube installed in the tube coupling hole 111;
    a variable end 220A which is bent at a portion coupled to the laryngeal mask piece and which is configured such that the variable end comes into contact with an inner wall of a patient's oral cavity; and
    an indication end which extends from the mouthpiece unit and which is configured to allow a patient's spontaneous breathing to be checked.

5. The laryngeal mask airway unit of claim 4, wherein the indication end of the tube further includes:
    a breathing indicating hole which protrudes from an outer surface of the indication end of the tube so as to be parallel to a longitudinal direction of the tube, a breathing monitoring window being formed along at least a portion of the breathing indicating hole;
    a first hole coupled to a first end of the breathing indicating hole such that air is introduced into the breathing indicating hole when a patient breathes in;
    a second hole which is connected to a second end of the breathing indicating hole such that air is discharged from the breathing indicating hole when the patient breathes out; and
    an indicator that is inserted into the breathing indicating hole and that moves in the breathing indicating hole due to a flow of air in the breathing indicating hole that is generated by a patient's breathing.

6. The laryngeal mask airway unit of claim 4, wherein the laryngeal mask piece of the laryngeal guide unit has a rear end portion which has the tube coupling hole, the rear end portion having a thickness greater than a tip portion of the laryngeal mask piece from which the support band protrudes.

7. The laryngeal mask airway unit of claim 4, wherein the breathing monitoring window has a light emitting surface which has a color or a light emitting material that is identifiable in a dark place.

8. A laryngeal mask airway unit for endoscopy, comprising:
    a laryngeal guide unit configured to be positioned in a patient's larynx inlet, wherein a support band is attached to and extends away from a first side of the laryngeal guide unit, the support band being configured to ensure an opened state of a patient's respiratory tract;
    an airway unit which includes a breathing tube connected to the laryngeal guide unit, the breathing tube being configured to supply outside air to the patient's respiratory tract;
    a mouthpiece unit that is configured to be positioned between a patient's teeth, wherein the breathing tube extends through a first passageway in the mouthpiece unit and wherein the mouthpiece unit includes a second passageway configured to receive an endoscopic probe, wherein the mouthpiece unit is configured to protect, from a patient's teeth, the breathing tube and an endoscopic probe extending though the second passageway; and
    a breathing indicator that is coupled to an end of the breathing tube that extends outward from the mouthpiece unit, wherein a movable member of the breathing indicator is configured to move when a patient is breathing.

9. The laryngeal mask airway unit of claim 8, wherein the breathing indicator comprises:
   a breathing indicating passageway having first and second ends coupled to an interior of the breathing tube, wherein the movable member is located in the breathing indicating passageway and wherein a patient breathing will induce a flow of air in the breathing indicating passageway that causes the movable member to move within the breathing indicating passageway; and
   a monitoring window along at least a portion of the breathing indicating passageway that allows one to see movement of the movable member within the breathing indicating passageway.

10. The laryngeal mask airway unit of claim 8, wherein the laryngeal guide unit is separate from the mouthpiece unit.

11. The laryngeal mask airway unit of claim 8, wherein an end of the breathing tube that is connected to the laryngeal guide unit includes a bent portion that is configured to contact an inner wall of a patient's oral cavity.

12. The laryngeal mask airway unit of claim 8, wherein a concave endoscope guide is provided on the first side of the laryngeal guide unit, the concave endoscope guide being configured to guide insertion of an endoscope towards a patient's esophagus.

13. The laryngeal mask airway unit of claim 8, wherein an air inlet hole that communicates with the breathing tube is formed on a second side of the laryngeal guide unit opposite the first side of the laryngeal guide unit.

14. The laryngeal mask airway unit of claim 13, wherein the air inlet hole comprises a concave depression formed on the second side of the laryngeal guide unit.

15. The laryngeal mask airway unit of claim 8, wherein a first end of the laryngeal guide unit to which the breathing tube is attached has a greater thickness than a second end of the laryngeal guide unit that is opposite the first end.

16. The laryngeal mask airway unit of claim 15, wherein an outer surface of the support band is inclined inward towards the second end of the laryngeal guide unit.

17. The laryngeal mask airway unit of claim 8, wherein a plurality of protrusions are provided on an outer surface of the support band, the plurality of protrusions being configured to increase friction between the support band and a patient's tissues to help immobilize the laryngeal guide unit relative to a patient.

18. A laryngeal mask airway unit for endoscopy, comprising:
   a laryngeal guide unit configured to be positioned in a patient's larynx inlet, the laryngeal guide unit comprising:
      a body having a breathing passageway therethrough;
      a support band that is removably attached to and extends away from a first side of the body, wherein the support band is configured to guide an endoscopic probe and to ensure an opened state of a patient's respiratory tract; and
      an air inlet provided on a second side of the body opposite the first side, the air inlet being coupled to the breathing passageway and comprising a concave depression formed on the second side of the body;
   a breathing tube connected to breathing passageway of the laryngeal guide unit; and
   a mouthpiece unit that is separate from the laryngeal guide unit and that is configured to be positioned between a patient's teeth, wherein the breathing tube extends through a first passageway in the mouthpiece unit and wherein the mouthpiece unit includes a second passageway configured to receive an endoscopic probe, wherein the mouthpiece unit is configured to protect, from a patient's teeth, the breathing tube and an endoscopic probe extending though the second passageway.

19. The laryngeal mask airway unit of claim 18, wherein a concave endoscope guide is provided on the first side of the body of the laryngeal guide unit, the concave endoscope guide being configured to guide insertion of an endoscope towards a patient's esophagus.

20. The laryngeal mask airway unit of claim 18, wherein a portion of the breathing tube adjacent where the breathing tube is connected to the breathing passageway of laryngeal guide unit is bent such that the breathing tube extends away from the laryngeal guide unit.

* * * * *